United States Patent [19]  [11]  4,396,778
Hager  [45] * Aug. 2, 1983

[54] PROCESS FOR CONVERTING DIALKYL SULFIDES TO ALKYL MERCAPTANS

[75] Inventor: Robert B. Hager, Collegeville, Pa.

[73] Assignee: Pennwalt Corporation, Philadelphia, Pa.

[ * ] Notice: The portion of the term of this patent subsequent to Jan. 26, 1999, has been disclaimed.

[21] Appl. No.: 331,486

[22] Filed: Dec. 17, 1981

Related U.S. Application Data

[63] Continuation-in-part of Ser. No. 183,705, Sep. 3, 1980, Pat. No. 4,313,006.

[51] Int. Cl.$^3$ .............................................. C07C 148/00
[52] U.S. Cl. ........................................................ 568/70
[58] Field of Search .......................................... 568/70

[56] References Cited

U.S. PATENT DOCUMENTS

| | | | |
|---|---|---|---|
| 2,816,146 | 12/1957 | Doumani | 568/60 |
| 2,910,506 | 10/1959 | Folkins et al. | 568/60 |
| 4,005,149 | 1/1977 | Kubicek | 568/70 |
| 4,059,636 | 11/1977 | Kubicek | 568/70 |
| 4,102,931 | 7/1978 | Buchholz | 568/73 |

FOREIGN PATENT DOCUMENTS

| | | | |
|---|---|---|---|
| 45-05531 | 2/1970 | Japan | 568/68 |
| 52-46203 | 11/1977 | Japan . | |
| 274095 | 9/1970 | U.S.S.R. | 568/70 |

Primary Examiner—Donald G. Daus
Assistant Examiner—M. C. Eakin

[57] ABSTRACT

A continuous process is provided for the vapor-phase preparation of $C_1$–$C_{18}$ alkyl mercaptans where a di $C_1$–$C_{18}$ alkyl sulfide is reacted with a molar excess of hydrogen sulfide at elevated temperature in the presence of a specified synthetic zeolite containing at least 10 percent by weight of an alkali metal, expressed as $Na_2O$.

9 Claims, No Drawings

PROCESS FOR CONVERTING DIALKYL SULFIDES TO ALKYL MERCAPTANS

BACKGROUND OF THE INVENTION

Related Applications

This application is a continuation-in-part of application Ser. No. 183,705 filed Sept. 3, 1980, now U.S. Pat. No. 4,313,006.

INTRODUCTION

This invention relates to a continuous vapor-phase process for the manufacture of alkyl mercaptans by reacting a dialkyl sulfide with hydrogen sulfide in the presence of a zeolite catalyst.

Alkyl mercaptans are produced commercially either by reacting an alkyl alcohol with hydrogen sulfide or by the addition of hydrogen sulfide to an alkene. In either case, the major by-product is the corresponding dialkyl sulfide, formed by the equilibrium reaction,

$$2RSH \rightleftharpoons RSR + H_2S.$$

There are commercial applications for certain dialkyl sulfides, but in most cases the dialkyl sulfides obtained as by-products in mercaptan-manufacturing processes are contaminated with a number of by-product impurities that make them difficult and uneconomical to purify, and they must, therefore, be disposed of as chemical waste. One possible method to reduce the volume of the by-product sulfide waste and to recover economic value from it, is to react it with hydrogen sulfide, thereby reconverting the major dialkyl sulfide component of the waste to alkyl mercaptan according to the reverse of the above equilibrium reaction. Several procedures for cracking symmetrical dialkyl sulfides with hydrogen sulfide to form the corresponding alkyl mercaptan are described in the prior art. Beach, et al. (U.S. Pat. No. 2,667,515) provides a process for converting dimethyl sulfide and hydrogen sulfide to methyl mercaptan over a catalyst consisting of 10% cadmium sulfide on alumina at about 400° C. Single-pass molar conversions to methyl mercaptan of about 59% are obtained. A Japanese patent (No. 77/046203) discloses a similar process using a tungsten trisulfide on alumina catalyst at 320°–450° C.

Kubicek (U.S. Pat. No. 4,005,149) discloses the use of carbon disulfide as a reaction promoter, in the presence of a sulfactive catalyst, such as cobalt molybdate on alumina, to enhance conversions to alkyl mercaptan at lower reaction temperatures. Molar ratios of dialkyl sulfide/carbon disulfide ranging from about 0.1/1 to about 50/1 are employed and the process is shown in the examples of the patent to be operable for dialkyl sulfides ranging from dimethyl sulfide to di-n-dodecyl sulfide (dialkyl sulfides up to $C_{40}$ are claimed). Catalyst temperatures in the range of about 400° F. (204° C.) to about 600° F. (316° C.) can be used. In U.S. Pat. No. 4,059,636, Kubicek further discloses the use of a supported phosphotungstic acid catalyst, a preferred embodiment being that carbon disulfide is also present in the reaction mixture to enhance the conversion of dialkyl sulfide to alkyl mercaptan at lower temperatures.

DEFINITIONS

The catalyst of this invention belongs to the family of zeolites which are synthetic aluminosilicates of well-defined chemical composition and physical structure.

The zeolite (or molecular sieve) catalysts are synthetic aluminosilicates characterized by high uniformity, well-defined pore size, large surface area, complete crystallinity and excellent reproducibility. Their structures are described in the Union Carbide booklet F-08 entitled, "Linde Molecular Sieve Catalysts," and D. W. Breck's textbook, "Zeolite Molecular Sieves", John Wiley & Sons (1974).

The basic structural units of synthetic zeolites are Si and Al atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each $AlO_4^-$ is negatively charged. The charge on these units is balanced by alkali metal cations e.g., $Na+$ or $K+$, in the as-synthesized zeolites. These cations may be partially exchanged with other metal cations.

Although many factors influence the catalytic activity of these zeolites, the three most important are: (1) the open framework structure with its attendant pore size, (2) the $SiO_2:Al_2O_3$ ratio of the framework, and (3) the cations.

As in most commercial catalytic conversion processes, however, only the large-pore zeolites having pore openings in the range of 7 to 10 Angstroms (Å) are useful. The two most preferred are Type X and Type Y zeolites. The Type L, more siliceous than Type X and Type Y, also has a pore size in this range. Type X, Y, and L are distinct, commercially available compositions, well known to those skilled in the art of zeolite chemistry. Type X has a chemical composition expressed in terms of oxide ratios of $Na_2O:Al_2O_3:2-3$ $SiO_2$ with a typical unit cell composition in the hydrated state of: $Na_{86}[(AlO_2)_{86}(SiO_2)_{106}].264H_2O$. Type Y, on the other hand, has a composition of $Na_2O:Al_2O_3:>3-6$ $SiO_2$. When the $SiO_2:Al_2O_3$ molar ratio is 4.8, the hydrated unit cell composition is $Na_{56}[(AlO_2)_{56}(SiO_2)_{136}].264H_2O$. Both of these zeolites crystallize in the cubic system.

An important building block of these zeolites is the sodalite cage, a truncated octahedron unit consisting of 24 (Si,AlO$_4$) units. In Type X and Type Y the sodalite cages are connected through 4 of the 8 hexagonal faces in a tetrahedral arrangement. The pores thus created are defined by a 12-member ring of oxygen atoms, approximately 7–9 Å size, opening into a central cavity of about 11 Å in diameter.

Type L zeolite is composed of cancrinite-type cages linked by double six-ring oxygen bridges producing a structure characterized by planar 12-ring pores having an opening of about 7.1 Å. Type L has a typical oxide formula of $Na_2O:Al_2O_3:6SiO_2.5H_2O$ with a typical unit cell composition in the hydrated state of $Na_9[(AlO_2)_9(SiO_2)_{27}].22H_2O$.

The preferred synthetic zeolites are Types X and Y because of their larger pore sizes. The ability of the Y type to withstand higher temperatures without losing its crystalline structure makes it the most preferred zeolite catalyst for this invention.

The zeolites, as prepared, generally contain as the cation about 13 percent by weight sodium (as $Na_2O$) or equivalent amount of other alkali metal.

STATEMENT OF THE INVENTION

This invention is a continuous, vapor-phase process for preparing high purity $C_1$–$C_{18}$ alkyl mercaptan, R—S—H, comprising reacting dialkyl sulfide, R—S—R, where R is $C_1$ to $C_{18}$ alkyl or $C_6$ to $C_{18}$ cycloalkyl, with a molar excess of hydrogen sulfide at elevated temperature in the presence of a Type X, Type Y or Type L zeolite containing at least 10% by weight of an alkali metal, expressed as $Na_2O$.

The following working example demonstrates this invention.

EXAMPLE

Crude diethyl sulfide (DES) obtained from a mercaptan plant distillation column-bottoms material (90% DES) and hydrogen sulfide ($H_2S$) were mixed and vaporized at a feed ratio of 10 moles of $H_2S$ per mole of DES in a preheater maintained at 260°–295° C. The vaporized mixture at a specified mole velocity of DES was passed continuously through the preheater at atmospheric pressure and through a reactor containing a heated catalyst bed consisting of ⅛-inch extrudate of a Type Y zeolite catalyst containing 13% by weight sodium (as $Na_2O$). The catalyst is a commercial material purchased from Union Carbide as Linde LZ-Y52. The reactor exit stream was analyzed by gas chromatography to determine the single-pass conversions of the crude DES to ethyl mercaptan. The reaction conditions and results are summarized in the following table.

TABLE

| Run No. | Mole Velocity* | Catalyst Bed Temp. °C. | % Conversions |
|---|---|---|---|
| 1 | 44 | 291 | 15.5 |
| 2 | 41 | 277 | 13.7 |

*Gram-moles of DES per kilogram of catalyst per 24 hours.

DISCUSSION-GENERIC

The invention described herein is a continuous, vapor-phase process for preparing high-purity $C_1$ to $C_{18}$ alkyl mercaptan by reacting a dialkyl sulfide with a molar excess of hydrogen sulfide at elevated temperatures in the presence of a Type X, Type Y or Type L zeolite containing at least 10% by weight of an alkali metal, expressed as $Na_2O$.

REACTANTS

The dialkyl sulfide used herein may be from any source but is preferably a crude by-product from an alkyl mercaptan, especially methyl or ethyl mercaptan, manufacturing process. The dialkyl sulfide is represented by R—S—R where R is a $C_1$–$C_{18}$ alkyl, preferably a $C_1$–$C_{12}$ alkyl group or a $C_{6-18}$ cycloalkyl group. The hydrogen sulfide reactant is obtained from any source and is used in excess of the stoichiometric quantity required to form the mercaptan with a dialkyl sulfide. A molar excess of hydrogen sulfide over the dialkyl sulfide is required for high conversions to alkyl mercaptan. The molar ratio of hydrogen sulfide to dialkyl sulfide preferably ranges from about 3/1 to 20/1, most preferably from 5/1 to 15/1.

REACTION CONDITIONS

Elevated temperatures in the range of from about 250° up to about 400° C. are used herein. The dialkyl sulfide reactant is preferably first vaporized by passage through a preheater. The reactants can be mixed in the preheater at the desired molar ratio and passed into the reactor containing the catalyst. The preheater temperature will generally be within the same temperature range as the catalyst bed i.e., about 250° to about 400° C., preferably from about 290° to 390° C. although lower preheat temperatures are useful. The pressure in the reactor will range from atmospheric to about 600 psig, perferably between about 50 and 350 psig.

The rate at which the dialkyl sulfide is passed over the zeolite catalyst ranges from about 10 to about 300 gram-moles, preferably about 30 to about 150 gram-moles of dialkyl sulfide per kilogram of catalyst per 24 hours. In commercial operation, a rate of about 50-150 pound-moles of dialkyl sufide per one-thousand pounds of catalyst per 24 hour day, is used.

In preferred operation, the crude product from the reactor is passed into a series of at least two continuous distillation towers where the excess unreacted hydrogen sulfide is separated in one tower and recycled to the reactor. High-purity alkyl mercaptan is separated as an overhead product in another tower and, optionally, any unconverted dialkyl sulfide is collected as a tower bottoms product and recycled to the preheater leading to the reactor.

It is an advantage of the zeolite catalyst that it is active in this process at relatively low temperatures and with short contact times obviating the need for a reaction promoter such as carbon disulfide.

I claim:

1. A continuous vapor-phase process for preparing high purity $C_1$–$C_{18}$ alkyl mercaptan, R—S—H, comprising reacting dialkyl sulfide, R—S—R, where R is $C_1$ to $C_{18}$ alkyl or $C_6$ to $C_{18}$ cycloalkyl, with a molar excess of hydrogen sulfide at a temperature within the range of about 250 to about 400° C. in the presence of a Type X, Type Y or Type L zeolite containing at least 10% by weight of alkali metal expressed as $Na_2O$.

2. The process of claim 1 wherein R is $C_1$ to $C_{12}$ alkyl and the alkali metal is sodium or potassium.

3. The process of claim 1 wherein R—S—R is a crude by-product from an alkyl mercaptan manufacturing process.

4. The process of claim 2 wherein the dialkyl sulfide and hydrogen sulfide are first preheated to a temperature within the range of about 250° to about 400° C.

5. The process of claim 4 wherein the pressure in the reactor ranges from atmospheric to 600 psig.

6. The process of claim 5 wherein the molar ratio of hydrogen sulfide to dialkyl sulfide ranges from 3:1 to 20:1.

7. The process of claim 6 wherein the rate at which the dialkyl sulfide is passed over the catalyst bed ranges from 10 to 300 gram-moles of dialkyl sulfide per kilogram of catalyst per 24 hours.

8. The process of claim 7 wherein the catalyst bed temperature ranges from about 290° to about 390° C. and the pressure in the reactor ranges from about 50 to about 350 psig.

9. The process of claim 7 wherein the unconverted dialkyl sulfide is continuously separated and recycled to the reactor to form additional alkyl mercaptan.

* * * * *